United States Patent
Ramabadran (10) Patent No.: US 11,147,506 B2
(45) Date of Patent: Oct. 19, 2021

(54) SLEEP DIAGNOSTIC SYSTEM AND METHOD

(71) Applicant: Somnomed Technologies Inc., Tampa, FL (US)

(72) Inventor: Arun Vikram Ramabadran, Tampa, FL (US)

(73) Assignee: Somnomed Technologies Inc., Tampa, FL (US)

( * ) Notice: Subject to any disclaimer, the term of this patent is extended or adjusted under 35 U.S.C. 154(b) by 61 days.

(21) Appl. No.: 16/428,356

(22) Filed: May 31, 2019

(65) Prior Publication Data

US 2019/0365315 A1  Dec. 5, 2019

Related U.S. Application Data (60) Provisional application No. 62/679,420, filed on Jun. 1, 2018.

(51) Int. Cl.
*A61B 5/00* (2006.01)
*A61B 5/087* (2006.01)
*A61B 5/1455* (2006.01)

(52) U.S. Cl.
CPC .......... *A61B 5/4818* (2013.01); *A61B 5/0022* (2013.01); *A61B 5/087* (2013.01); *A61B 5/14552* (2013.01); *A61B 5/6823* (2013.01); *A61B 5/6831* (2013.01); *A61B 5/6898* (2013.01); *A61B 2562/0204* (2013.01); *A61B 2562/0219* (2013.01)

(58) Field of Classification Search
CPC .... G16H 10/60; A61B 5/4818; A61B 5/0022; A61B 5/0002; A61B 5/4806; A61B 5/0024; A61B 5/4809; A61B 5/0826; A61B 5/14552
See application file for complete search history.

(56) References Cited

U.S. PATENT DOCUMENTS

| | | | |
|---|---|---|---|
| 2013/0144190 A1 | 6/2013 | Bruce et al. | |
| 2014/0051942 A1* | 2/2014 | Gillette | A61B 5/01 600/301 |
| 2014/0128697 A1* | 5/2014 | Parfenova | A61B 5/02007 600/328 |
| 2017/0079580 A1* | 3/2017 | Moore at al. | G16H 40/63 |
| 2017/0239418 A1* | 8/2017 | Levine | G06F 19/00 |
| 2017/0347951 A1 | 12/2017 | Gollakota et al. | |

OTHER PUBLICATIONS

European Patent Office, International Search Report in International Patent Application No. PCT/US2019/034897, 7 pp. (dated Jul. 15, 2019).

European Patent Office, Written Opinion in International Patent Application No. PCT/US2019/034897, 9 pp. (dated Jul. 15, 2019).

* cited by examiner

*Primary Examiner* — Carl H Layno
*Assistant Examiner* — Aya Ziad Bakkar
(74) *Attorney, Agent, or Firm* — Leydig, Voit & Mayer, Ltd.

(57) ABSTRACT

A system and method for conducting a sleep test includes initiating a sleep test script, and providing the script to a patient. Testing hardware is shipped from a provider to the patient, and instructions are provided to the patient for connecting the testing hardware to a mobile computing device. A mobile sleep application is downloaded and installed onto the mobile computing device. The testing hardware is connected to the mobile computing device, and the sleep test is conducted using the mobile sleep application operating on the mobile computing device.

10 Claims, 10 Drawing Sheets

FIG. 18 ial Patent Application No. 62/679,420, filed on Jun. 1,
SLEEP DIAGNOSTIC SYSTEM AND METHOD

CROSS-REFERENCE TO RELATED APPLICATIONS

This patent application claims the benefit of U.S. Provisional Patent Application No. 62/679,420, filed on Jun. 1, 2018, which is incorporated herein in its entirety by this reference.

BACKGROUND OF THE INVENTION

Approximately 65 Million American adults suffer from sleep disordered breathing conditions where 1 in 5 adults has obstructive sleep apnea or central sleep apnea conditions. Of this population, approximately only 1 in 15 adults are properly screened, tested and then treated for this condition, but leaves a large gap of patients untested. As the population continues to increase and obesity prevalence increases, sleep disordered breathing conditions will continue to rise as a medical condition required to be treated. Untreated sleep disordered breathing conditions has been shown to increase chance of heart disease, stroke, diabetes, hypertension, depression, cancer, and other medical conditions.

The current method of evaluating and screening patients for sleep apnea utilizes two different testing methodologies, either an in-lab based monitored sleep test or an unmonitored home sleep test. For many years the gold standard of sleep diagnostic testing was determined to be an in-lab study, but due to customer convenience and cost to the patient, home sleep testing was introduced to the market approximately 5 years back and has been gaining acceptance through the medical community. Though a home sleep test cannot evaluate patients for the full spectrum of sleep disorders, it is an effective tool in screening patients for obstructive sleep apnea. Most devices in this space consist of a small electronic module capable of detecting body signals such as, pulse rate, blood oxygen level, breathing effort, and nasal air flow.

The data from the overnight sleep test is stored on the module and the patient either ships the unit back to the service provider or drops the unit off physically. Once the provider receives the device, they will manually download the data from the device into a scoring program capable of viewing and commenting on various sleep markers. Once the full night's data is evaluated, the results of the data are summarized and sent to a board certified sleep physician in order to review and sign off on the report and treatment plan. This report is then typically sent back to the ordering physician and/or patient directly for further review. The following steps summarize the typical process, which includes an order or script from a physician to a sleep lab or home study provider, contacting the patient to inform them of the script receipt and scheduling of test, the provider obtaining authorization from the patient's insurance company, if required, picking up or shipping a home sleep test device from the provider office to the patient. The patient then utilizes the device for 1-2 nights to acquire data, and either drops off or ships device back to provider. The provider scores data and sends to sleep physician for review. The provider then sends signed results back to the referring physician.

BRIEF SUMMARY OF THE INVENTION

With the proliferation of smart phone use globally, there is a consensus that introducing medical based testing through the smart phone would be able to screen and reach a larger section of the population more cost effectively. The current estimate of smart phone users globally by the end of 2018 is expected to be 2.5-3 billion people.

The present disclosure describes an alternative and novel system and method for home sleep testing. In one embodiment, patients are diagnosed utilizing a patient's smart phone to conduct the sleep test at home by collecting, preprocessing and communicating sleep data and conclusions between the patient and the doctor or data center that processes the data. This novel approach includes at least the following steps:

(a) Order from physician to sleep lab or home study provider, which is optional and may also be initiated by the prospective patient's desire to determine their quality of sleep;

(b) Patient is contacted to inform them of the script receive and scheduling of test, which can alternatively include the patient's downloading of a smartphone app and order of any testing hardware that is required;

(c) Provider obtains authorization from their insurance company or patient pays cash for test;

(d) Provider ships out ancillary leads to plug into their smart phone jack;

(e) Patient downloads app with single use license from the lab;

(f) Data is automatically uploaded from patients phone to a scoring algorithm stored in the cloud and scored;

(g) Summary report is generated for physician to sign off on, which is optional and may be replaced, for certain tests and in certain countries, with an automated processing and report form the sleep analysis system server, and (h) Results are transmitted to patients physician and sent back via smart phone app to patient.

It is noted that, globally, in other markets outside the US, a physician sign off may not be required, which may also be the case or an option for patients that pay for their service without contribution from an insurance company. The current home sleep test units and sensors are shipped to a patients home and typically weigh 3 lbs or more with the unit, sensors and packaging. The new implementation, as described in the present disclosure, saves on shipping costs by only having to ship out the sensors themselves, which reduces shipping costs to less than 0.25 lb. In order to provide home sleep testing to a larger percentage of the population, a mobile app based sleep testing solution can provide effective testing, scoring, and clinical results to patients in a cost effective manner than existing portable sleep testing units.

In one aspect, therefore, the present disclosure describes a method for conducting a sleep test. The method includes initiating a sleep test script, and providing the script to a patient. Testing hardware is shipped hardware from a provider to the patient, and instructions are provided to the patient for connecting the testing hardware to a mobile computing device. A mobile sleep application is downloaded and installed onto the mobile computing device. The testing hardware is connected to the testing hardware and to the mobile computing device, and the sleep test is conducted using the mobile sleep application operating on the mobile computing device.

In another aspect, the present disclosure describes a sleep diagnostic system that includes a set of testing hardware, the testing hardware comprising: a plurality of sensors adapted for mounting onto a patient's body, the plurality of sensors configured to provide signals indicative of patient parameters, and a sensor interface device, the sensor interface device being connectable via mechanical and electrical connections to the plurality of sensors, the sensor interface device being adapted to further mechanically and electrically connect to a mobile computing device. A mobile sleep application stored on non-transient computer media includes computer executable instructions that are executable by a processor of the mobile computing device, and a cloud environment operating on at least one cloud server, the at least one cloud server being communicatively connected with the mobile computing device for data transfer therebetween. During a sleep test, information acquired from the plurality of sensors is stored as a data set on a memory device of the mobile computing device and transmitted to the cloud environment upon test completion for processing.

In yet another aspect, the disclosure describes a method for conducting a sleep test for a patient at home. The method includes receiving at a provider a prescription from a physician relative to a patient for conducting a sleep test, collecting patient information at the provider relative to the patient, providing information to the patient from the provider relative to downloading and installing onto a mobile computing device of the patient a sleep monitoring mobile application sending to the patient from the provider a set of testing hardware, the set of testing hardware including a plurality of external sensors and a sensor interface device, the plurality of external sensors being connectable via wired connections to the sensor interface device, and the sensor interface device being connectable via wired connection to the mobile computing device of the patient, wherein the patient is adapted to connect the set of testing hardware to the mobile computing device, conduct a sleep test, and acquire a set of data that is stored in encrypted form within the sleep monitoring mobile application, and receiving at the provider the set of data after completion of the sleep test.

DETAILED DESCRIPTION OF THE INVENTION

With the proliferation of smart phone use globally, there is a consensus that introducing medical based testing through the smart phone would be able to screen and reach a larger section of the population more cost effectively. The current estimate of smart phone users globally by the end of 2018 is expected to be 2.5-3 billion people.

The present disclosure describes a system and method for conducting a home sleep test model to diagnose patients utilizing a patient's smart phone to conduct the sleep test at home by collecting, preprocessing and communicating sleep data and conclusions between the patient and the doctor or data center that processes the data.

Figure 1:
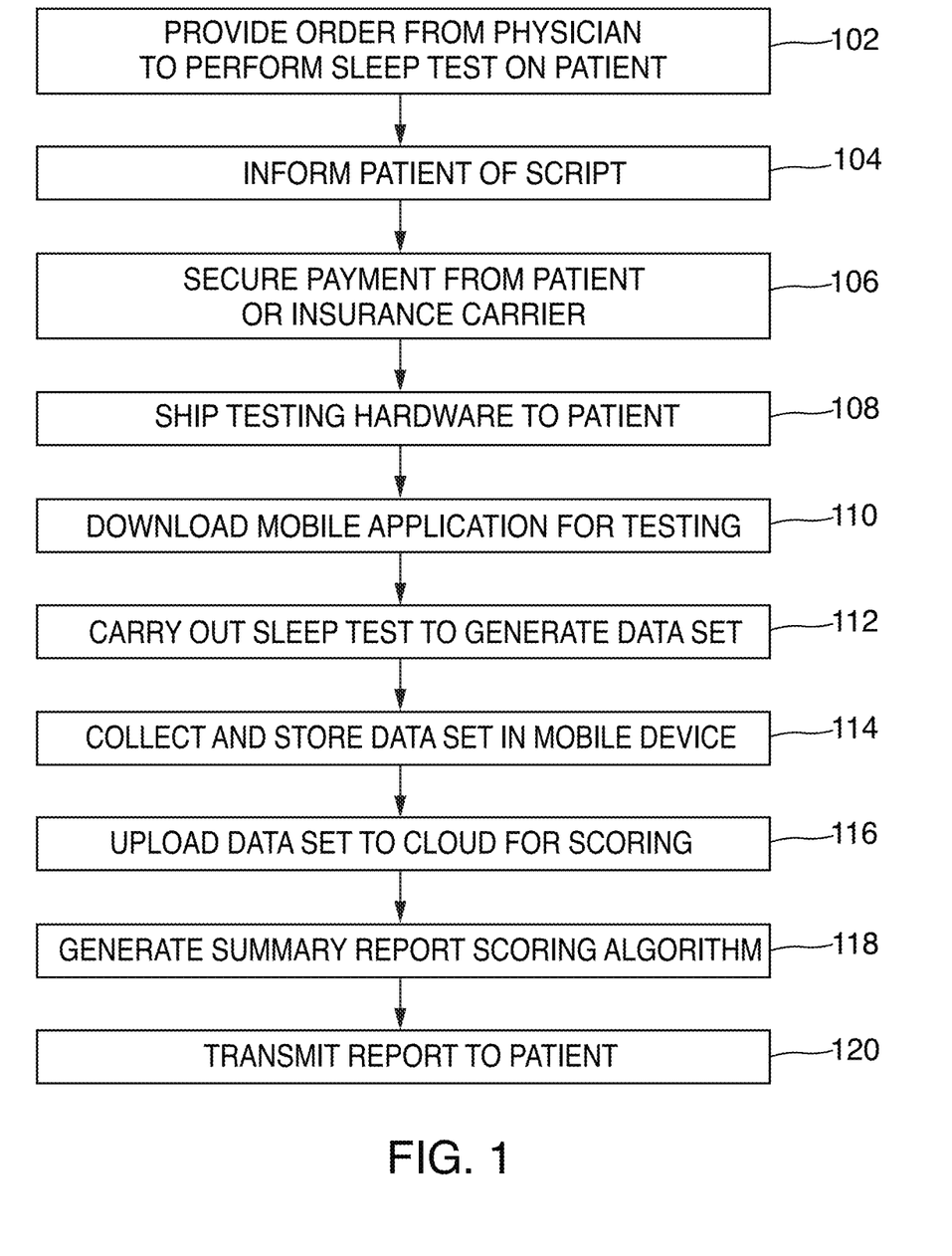
FIG. 1 is a flowchart for a method in accordance with the disclosure.

A method for conducting the sleep test in accordance with the disclosure is shown in the flowchart of FIG. 1. The method includes providing or acquiring an order or script from a physician to a sleep lab or home study provider to perform a sleep test on a patient at 102. It is contemplated that the physician order may be optional for situations where the patient may initiate a test on their own if they desire to determine the quality of their sleep. The patient is contacted to inform them of the script at 104. Patient contact at 104 may also convey other useful information to the patient such as instructions for receiving and scheduling a sleep test, directions for downloading a smartphone app that will be used during testing, instructions for fitting and wearing the various sensors, directions on setting up the test, information on how sleep data will be processed and the results of the test communicated to the patient, and other useful and relevant information. Patient contact may also be used to receive information on the appropriate size and type of sensors that will best suit the patient.

If applicable, the provider may obtain authorization from the insurance company of the patient, or patient may pay for the test themselves at 106. The provider may then ship to the patient hardware in the form of a sensor interface device, the sensors themselves, and other supplies needed for the patient to use the sensors at 108. Before conducting the test, the patient can download the provider's mobile phone application at 110, which can include a single-use license from the provider. The patient can then carry out the test at 112, which will result in a body of data from the various sensors being acquired and saved in the mobile phone via the mobile application at 114. The body of data, or data set, is then uploaded from the patient's mobile phone to a secure cloud at 116, where a scoring algorithm that is stored in the cloud can sort, normalize and score the data automatically. A summary report is generated at 118 that is made available for a physician to view and authorize. It is contemplated that the physician's review and authorization is optional and may be replaced, for certain tests and in certain countries, with an automated processing and report form the sleep analysis system server operating in the cloud. The results are then transmitted to the patient via the mobile app at 120.

It is noted that, globally, in markets outside the U.S., a physician sign off may not be required, which may also be the case or an option for patients that pay for their service without contribution from an insurance company. The current home sleep test units and sensors are shipped to a patients home and typically weigh 3 lbs or more with the unit, sensors and packaging. The new system and method in accordance with the disclosure leverages the computing and communication capabilities of a mobile computing device such as a mobile phone, which also include internal sensors, and augments those capabilities with other sensors that are sent to the patient and that are connectable to the mobile phone. In this way, shipping costs and complexity for conducting the test is reduced to the point where the patient can administer the test on themselves at home.

Figure 2:
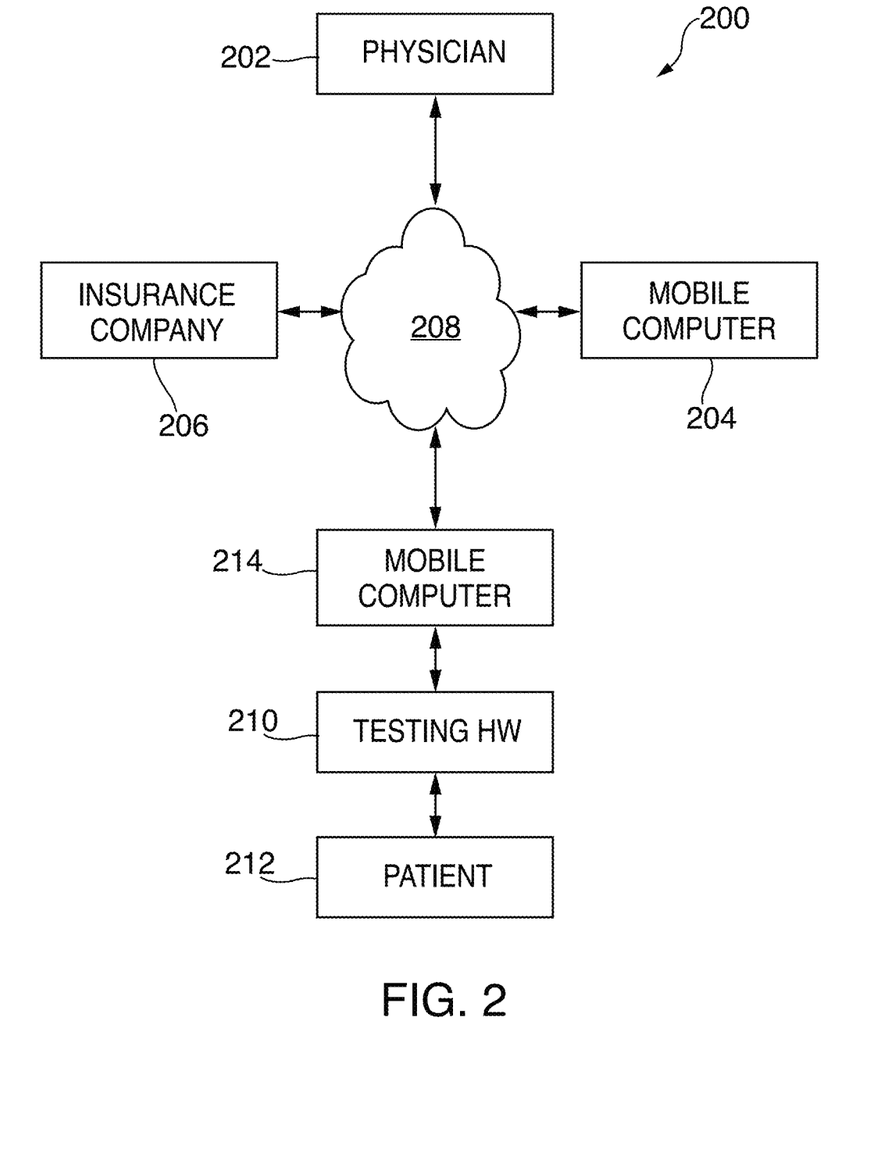
FIG. 2 is a schematic for a sleep diagnostic system in accordance with the disclosure.

A schematic for a sleep diagnosis system 200 in accordance with the disclosure is shown in FIG. 2. The system 200 includes the various parties that may participate in the method described and shown in FIG. 1, which can include a physician 202, a provider 204, optionally, an insurance company or carrier 206, and a secure cloud environment 208. The cloud 208 may facilitate communication and exchange of information between the physician 202, the provider 204 and the insurance carrier 206. As described above, the physician 202 may generate a prescription for a sleep test, information for which may be disseminated to the provider 204 and the insurance company 206 by traditional channels, for example, mail or facsimile transmission, or may alternatively be transmitted electronically through the cloud 208 in a secure fashion. Authorization of the prescription, and generation of an order with the provider 204 may also be shared in the same fashions to generate a shipment of instructions and sensor hardware 210 from the provider 204 to a patient 212. The sensor hardware 210, which after use may be returned to the provider 204, interfaces between the patient 212, to acquire vital information about the patient during the sleep test, and the patient's mobile computing device 214, for example, smart phone, which acquires and transmits the data thus acquired to the cloud 208.

In order to provide home sleep testing to a larger percentage of the population, a mobile app based sleep testing solution installed and operating on the mobile computer 214 provides effective testing, scoring, and clinical results to patients in a cost effective manner than existing portable sleep testing units.

In one embodiment, the testing hardware 210 can include sensors and appropriate wiring to connect the sensors to the mobile computer 214. These sensors can include both external sensors mounted onto the patient's body, and also internal sensors of the mobile computer. In the illustrated embodiment, external sensors can include a blood oxygen level sensor, a breath rate sensor, and a nasal air flow sensors, all with adapters that allows connection of the sensors to clothing or around a patients face. These sensors, as well as onboard sensors of the mobile device, can provide sufficient information for a diagnosis based on the results of a sleep test. Various examples of external sensors that are contemplated for use in a system in accordance with the disclosure are described in the paragraphs that follow.

Before turning to the sensors, various system diagrams on the connections and operation of the mobile computer will be described. A block diagram for a sleep diagnosis system 300 is shown in FIG. 1. The system 300 includes external sensors such as a nasal air flow sensor or nasal cannula 302, a respiratory rate sensor 304, and a blood oxygen level sensor 306, examples of which are shown in FIGS. 5, 4 and 6, respectively.

Figure 7:
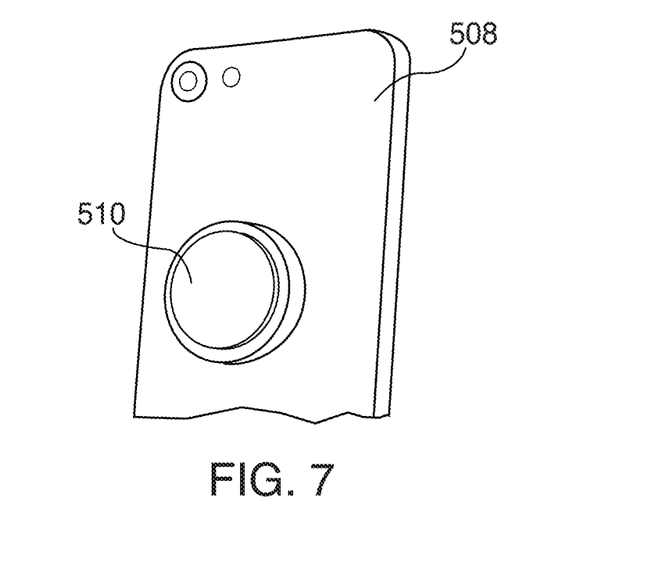
FIG. 7 is a mobile device mount in accordance with the disclosure.

For example, the respiratory sensor 304 may include an adjustable belt 502 word around the torso of the patient. The belt 502, shown in FIG. 4, may include a piezo-sensor 504 that provides a signal when the patient takes a breath. A holster 506 may also be connected to the belt to mount the smart phone 508 (see FIG. 7) via a magnetic clip 510 to the belt 502 and, thus, to the patient during the test. The breath rate and chest movement are measured by a piezo electric strain gauge mounted to a flexible/elastic belt assembly. As the chest moves during breathing, the sensor will pick the breath movement and convert this signal to an electrical voltage which can be recorded by the cell phone utilizing the app.

Figure 5:
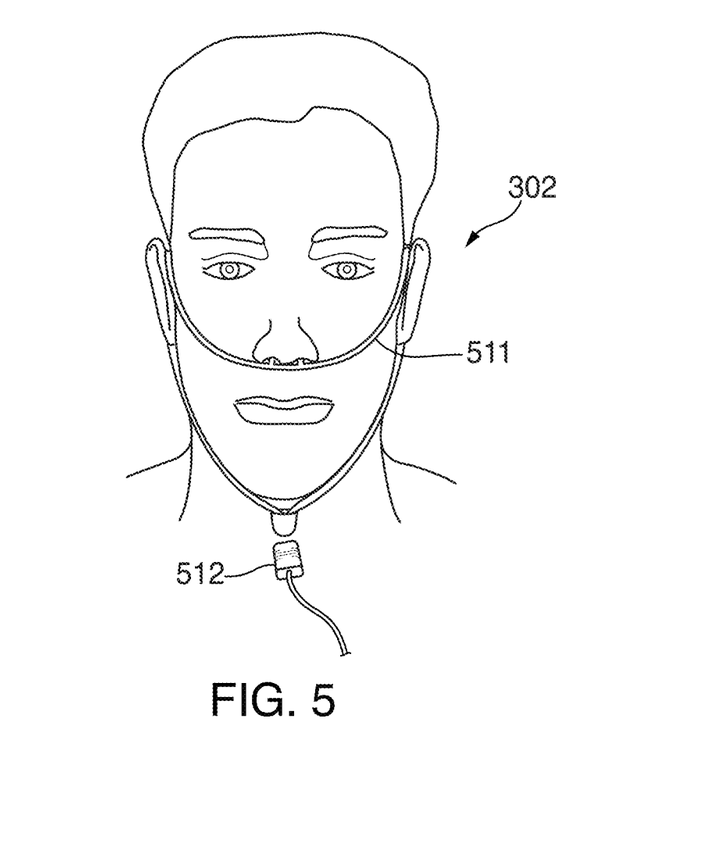
FIG. 5 is an outline view of a nasal air flow pitot tube assembly in accordance with the disclosure.

The nasal cannula 302 shown in FIG. 5 may include tubing 511 that provides air to the patient and also a flow meter 512 for measuring the breathing rate of the patient during the test. The nasal air flow pitot tube assembly also utilizes a piezo electric sensor to detect the nasal air flow from the patient, and can further include a pressure transducer or pressure transmitter that detects the flow of air as the subject is breathing during sleep. These signals are converted to voltage signals, which can be recorded by the cell phone utilizing the app. This new version of the air flow sensor will have over ear pieces that is part of the tubing assembly, which keeps the nasal cannula within the nostrils without coming out during sleep or head movement. Traditional cannulas just wrap the tubing over the patients ears, but patients manually will have to apply tape onto their faces to keep the tubing in place during the nights study.

Figure 6:
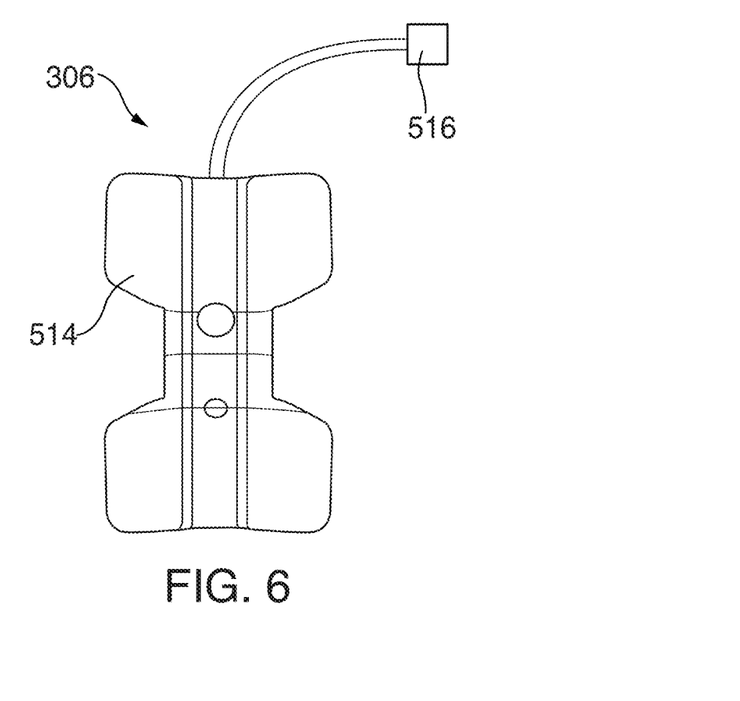
FIG. 6 is an outline view of a pulse oximeter in accordance with the disclosure.

Finally, the blood oxygen sensor 306, shown in FIG. 6, may include a finger sensor 514 that measures blood oxygen level during the test and provides a signal to a connector 516. The 02 is detected by a pulse oximeter utilizing light in different wavelengths to detect the flow of oxygenated blood, this will provide output in a current waveform which will be recorded by the cell phone utilizing the app.

Figure 3:
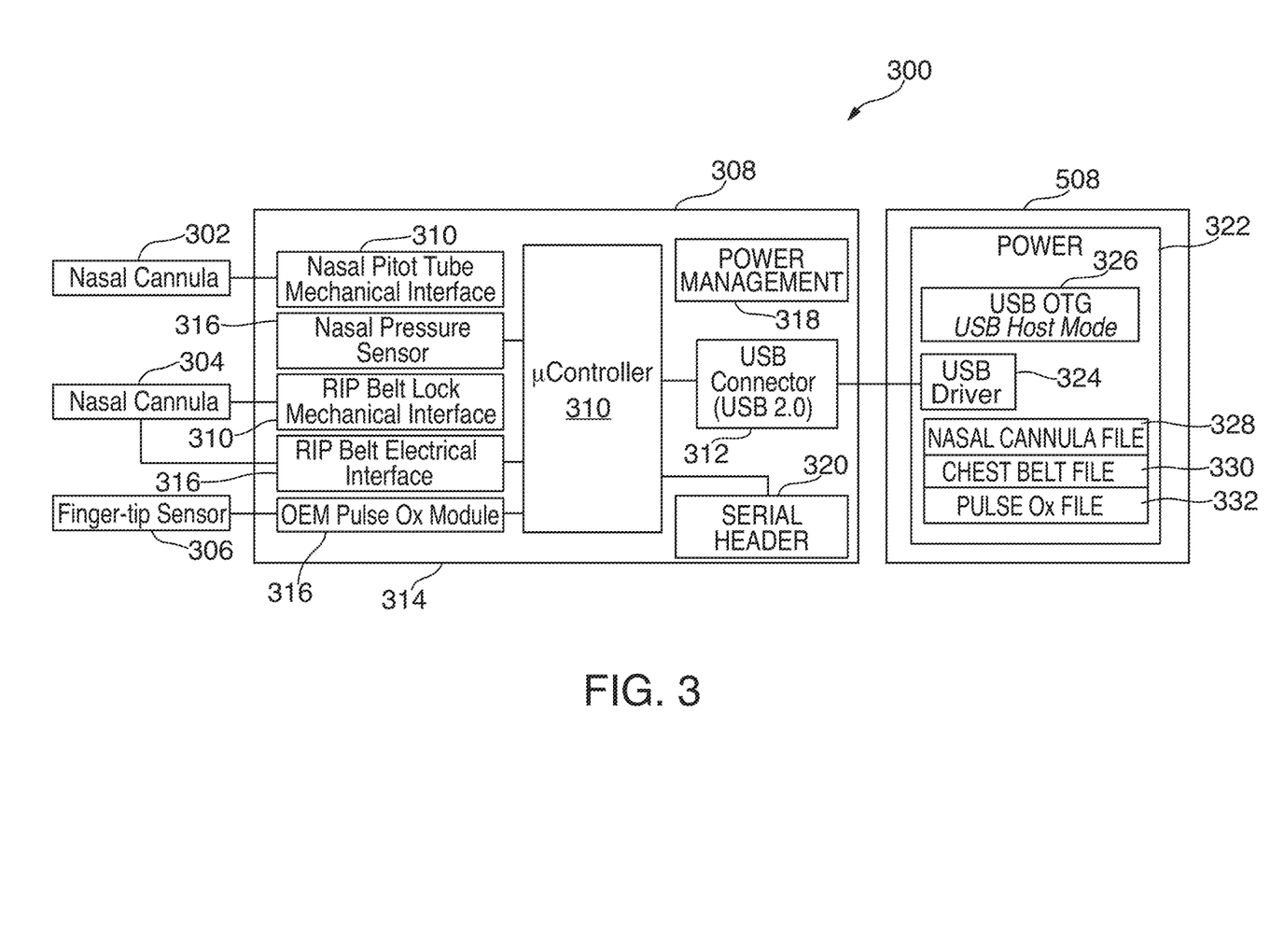
FIG. 3 is a diagram for one embodiment of a sleep diagnostic system in accordance with the disclosure.
Figure 4:
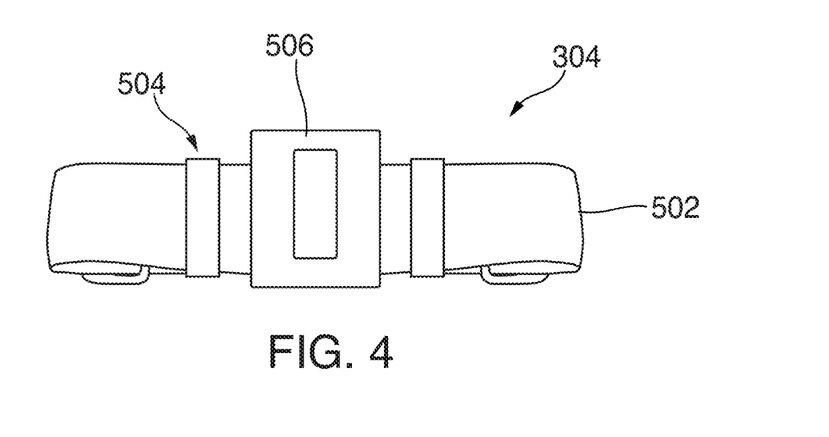
FIG. 4 is an outline view of a piezo sensor in accordance with the disclosure.
Figure 8:
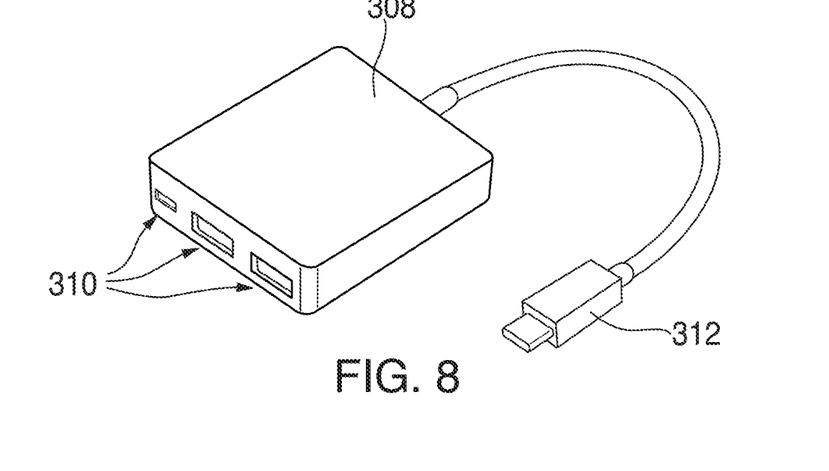
FIG. 8 is an exemplary embodiment of a sensor interface device in accordance with the disclosure.

These and other sensors are connected via wiring to a sensor interface device 308, an example of which is shown in FIG. 8, and block, diagram for which is shown in FIG. 3. The sensor interface device 308 fulfills a dual role—it provides a mechanical connection between the sensors 302, 304 and 306, through sensor plugs 310 (FIG. 8), and the mobile computer, through a connector plug 312 while also powering the sensors, and it also includes an integrated controller 310 that includes the various sensor transfer functions to decode sensor signals and provide digital information indicative of the sensor signals to a USB (universal serial bus) interface 312.

More specifically, the interface device 308 includes a chassis 314 onto which the micro-controller 310 is mounted and operates. Power is provided from the smartphone 508 through the USB interface 312 to power the sensors and the controller. The mechanical interfaces or plugs 310 are attached to the chassis 314, and signals from the sensors are provided through electrical interfaces 316 directly to the micro-controller 310. Onboard power management devices 318 for conditioning and controlling electrical power operating the various components, and headers 320 for managing the transfer of digital information to the smartphone 508 can also be used on the chassis 314.

The smartphone 508 may include an application environment 322 that includes a USB interface or driver 324 operating to convey information containing sensor readings from the micro-controller 310 into the environment for processing and storage. Specifically, a host controller 326 may receive, categorize and store information from the various sensors into dedicated memory locations for each sensor, for example, a nasal air flow data location 328, the breathing sensor data location 330, and the blood oxygen data location 332 while the test is underway. The host controller 326 may also monitor and record information during a test from onboard sensors of the smartphone 508, and store information from those onboard sensors as well in dedicated memory locations.

It should be appreciated that the sleep mobile application, and also any other modules discussed herein, in certain embodiments, may be embodied as a computer application or program. The computer program may exist in a variety of forms both active and inactive. For example, the computer program can exist as software program(s) comprised of program instructions in source code, object code, executable code or other formats; firmware program(s); or hardware description language (HDL) files. Any of the above can be embodied on a computer readable medium, which includes computer readable storage devices and media, and signals, in compressed or uncompressed form. Exemplary computer readable storage devices and media include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present teachings can be configured to access, including signals downloaded through the Internet or other networks. Concrete examples of the foregoing include distribution of executable software program(s) of the computer program on a CD-ROM or via Internet download. In a sense, the Internet itself, as an abstract entity, is a computer readable medium. The same is true of computer networks in general.

With respect to onboard sensors, for example, the mobile application may further utilize the phone gyroscope, the body position will also be determined during sleep. This is handled through a holding plate 510 (FIG. 7) on the belt 502 (FIG. 4) which keeps the phone 508 on the patient's chest during the nights study. Further, utilizing the built in microphone of the smartphone, we can also capture sounds typically during a patients sleep patterns which is typically snoring. This snoring signal would overlay on the breathing effort to compare the signals. Depending on the location of the phone on the patient's body, an accelerometer may also be used to measure vibration caused by the snoring in case the microphone is muffled under the patient's covers while sleeping.

The various external sensors may be integrated into one single connector for an iPhone lightning jack or micro usb connector capable of providing power to all four sensors through the phone. These two connector types would support all standard smart phone jacks. It is also a further development to isolate the individual sensors into a separate battery based Bluetooth module to enable communications between the sensors and the app utilizing wireless communications. The phone circuit power will also provide any necessary voltage for the individual sensors. There will be a separate pigtail connectors coming off the base unit with iPhone lightning jack, micro usb, or other so that this single connector can be used with multiple phone types.

It is a further embodiment of the present disclosure to have a licensing key server which will allow the sleep service providers to upload information on a patient including name, address, date of birth, contact info, email, Insurance info etc. After a patient profile has been created, the sleep lab personnel can then create a unique security key which will be valid for a single or two night usage depending on selection which will then be texted/emailed to the patient directly. This unique key will have to be entered into the app before further functions are enabled and the sleep diagnostic test can begin.

Figure 9:
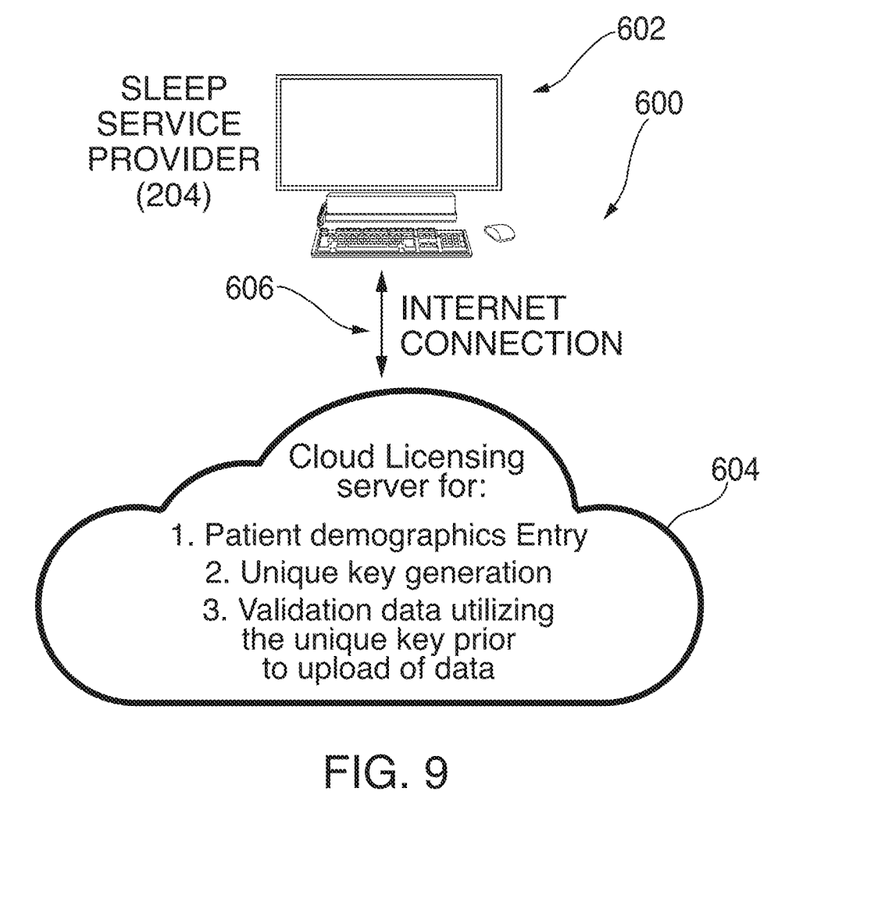
FIG. 9 is a schematic diagram of a provider system in accordance with the disclosure.

An exemplary embodiment of a system that can accomplish having all data within the app to remain encrypted for security HIPPA compliance of patient specific medical data is shown in FIG. 9, which illustrates a system 600 for secure transfer of data. In this embodiment, all PHI (personal health information) will remain encrypted within the app and in all transmissions between the mobile phone and the cloud servers utilized to score and create a clinical report will remain encrypted. The encapsulation of this PHI data will be created using "trusted" security keys between each individual app and the cloud utilizing specific secret keys to establish and ensure data integrity and proper transfer. Specifically, a computer system 602 of the service provider may communicate with a server 604 in the secure cloud, for example, the cloud 208 (FIG. 2) through a direct internet connection 606. The server 604 may track patient information, generate unique keys, and validate any patient data received against the patient information and after verifying the key to ensure patient confidentiality and data accuracy.

A further aspect of the present disclosure is a mobile application that provides screens or user interfaces to allow the user to ensure security by utilizing a secret key, provide instructional details on how to connect the sensors to their body and phone, to provide tools to determine whether or not the sensors are functioning and/or are connected properly, to validate whether the phone collected sleep data properly and consistently during a sleep session or over a predefined period, for example, overnight, provide diagnostic tools and messages to provide feedback to the user while either collecting, processing, or uploading data, to provide a report formatted with the test results through the app once scored, and other features. Exemplary views of such user interfaces are provided in FIGS. 10-17.

Figure 10:
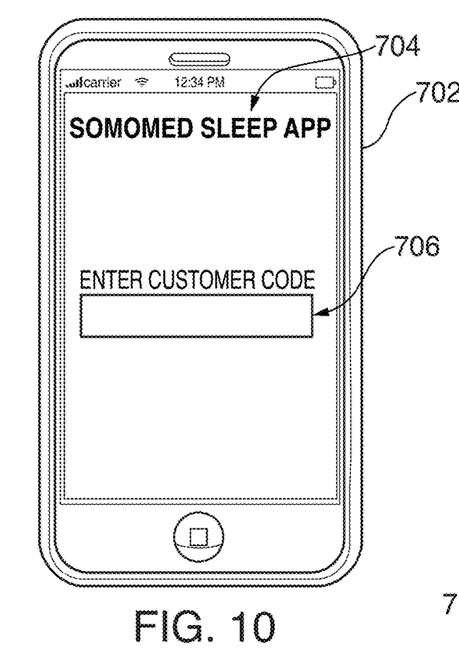
FIGS. 10-17 are exemplary user interface screens for a mobile application in accordance with the disclosure.

More specifically, an initial screen 702 is shown in FIG. 10. The initial screen 702 and the remaining screens that are discussed herein may be coded in any appropriate method such that they are presented to a user for input and output of information before, during and after the test is conducted. With reference to the initial screen 702 shown in FIG. 10, the screen may include a title block 704 and an entry field 706 into which the user may enter, for example, using the smartphone's text input functionality, a customer code or other identifier provided to the patient by the provider. The customer code at 706 may also include or embody an encryption key and also license information for a single use of the app by the patient. Upon entry of the customer code, the patient is presented with a patient information screen 708, shown in FIG. 11.

Figure 11:
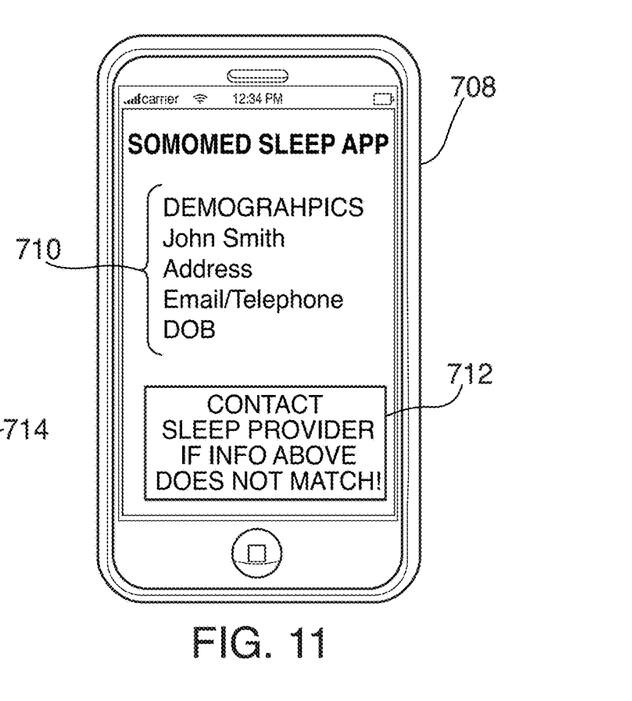
Figure 12:
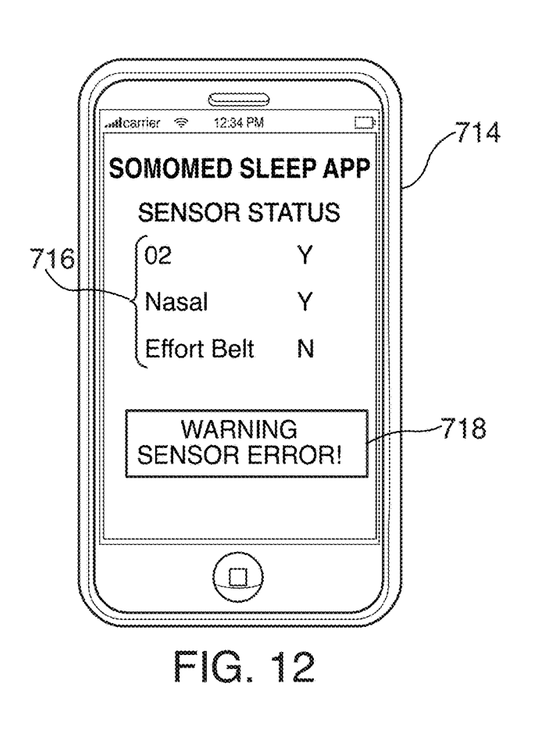

The patient information screen 708 presents to the patient the demographic and identifying information 710 that the provider has on file for the particular patient, for verification, and prompts the user to contact the provider using a banner 712 to contact the provider in the event information at 710 is in any way inaccurate. Upon confirmation of the patient's information by the patient, an initiation screen 714 is presented. At the initiation screen, the application may first diagnose the connective state and operation of the various external sensors that will be used during the test, and provide a list or dashboard 716 that lists the various sensors that are required and indicate an online state or condition of each sensor. In the illustrated example, a "Y" or "N" is used to qualitatively characterize the condition of each sensor, but any other method can be used that includes visible and/or audible prompts generated by the application. In the event one sensor is not reporting a condition that is suitable to initiate the test, a warning 718 is displayed. The warning may be selectable to launch a tutorial to aid the user in properly connecting the sensors to their smartphone using the testing hardware that was supplied to the patient by the provider.

Figure 13:
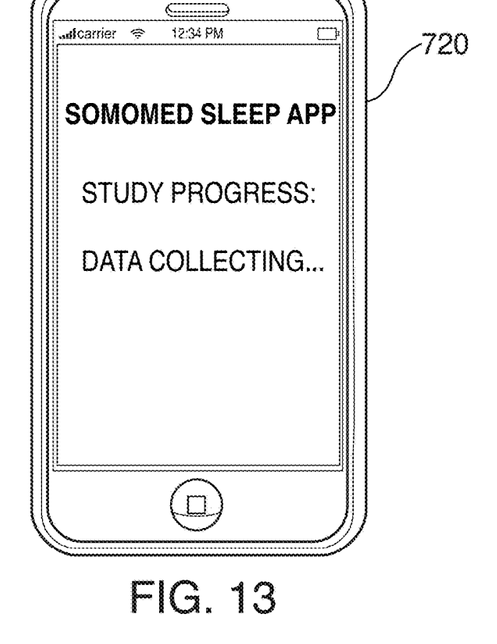
Figure 14:
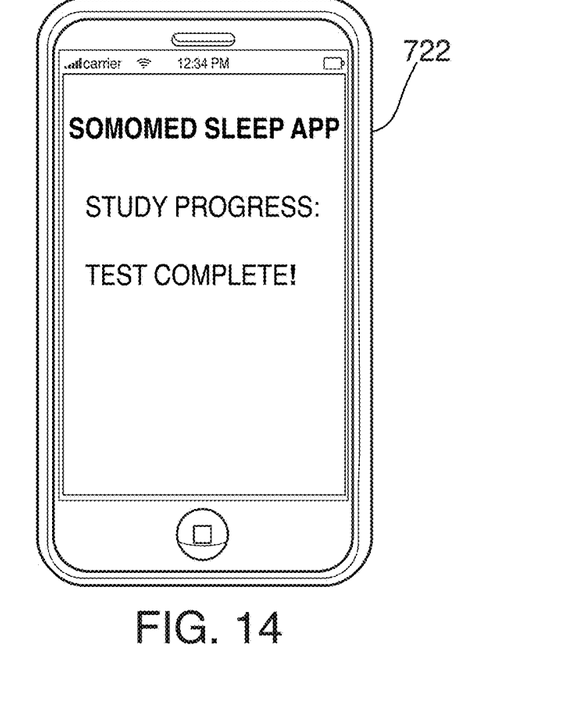
Figure 15:
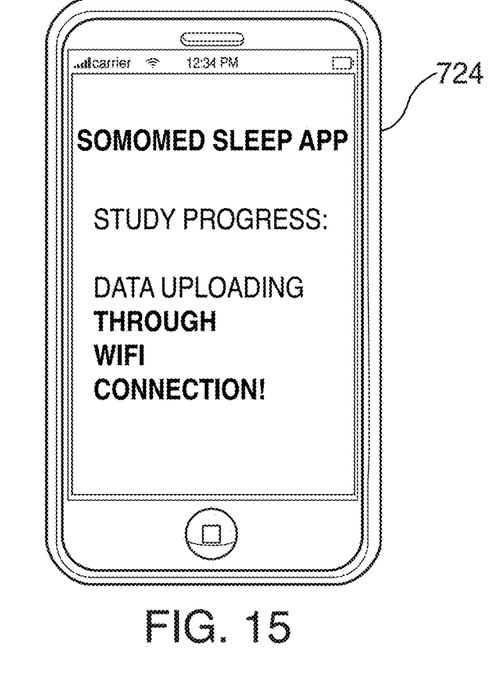
Figure 16:
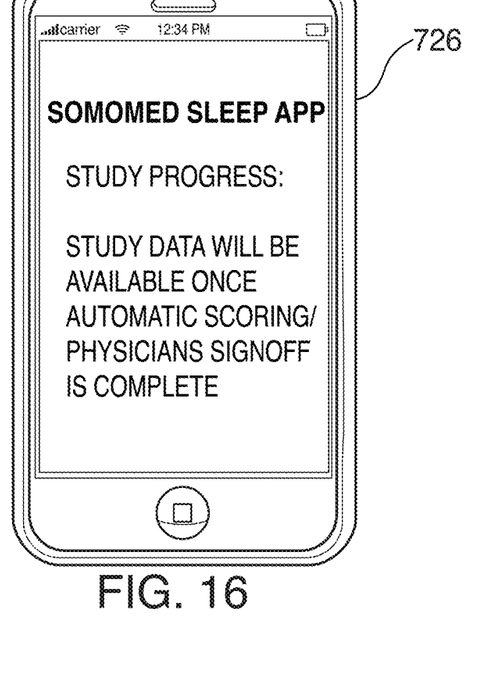
Figure 17:
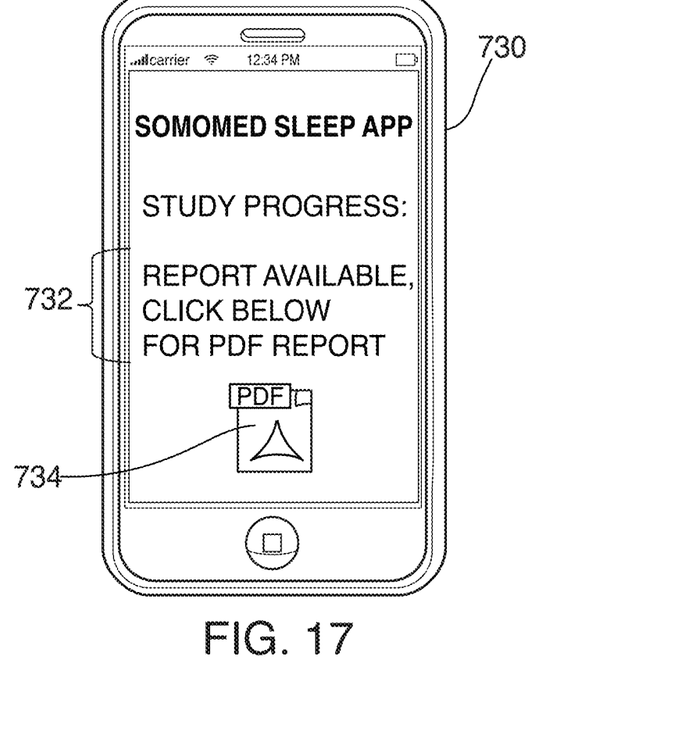

When all the sensor warnings have been cleared, for example, by ensuring that all sensors are connected properly, the test may be initiated. During the test, a progress screen 720 as shown in FIG. 13 may inform the user that data is being collected. Upon completion of the test, a completion screen 722 may inform the user that the test has been completed, as shown in FIG. 14, and that the collected data is being uploaded at a status screen 724 in a secure fashion, as shown in FIG. 15. Upon successful uploading of the data, an information screen 726 may provide information to the patient through a banner 728 or other method, informing the patient of the signoff process data processing will follow, e.g., that the data will become available after a physician's signoff, as shown in FIG. 16. When the data processing and report compilation is complete, the application may provide a notification to the user to access the application and, in the application, provide a results screen 730 that includes a banner 732 informing the user that the data processing is complete and providing a download link 734 for the user to download, save and view the results of the test.

Figure 18:
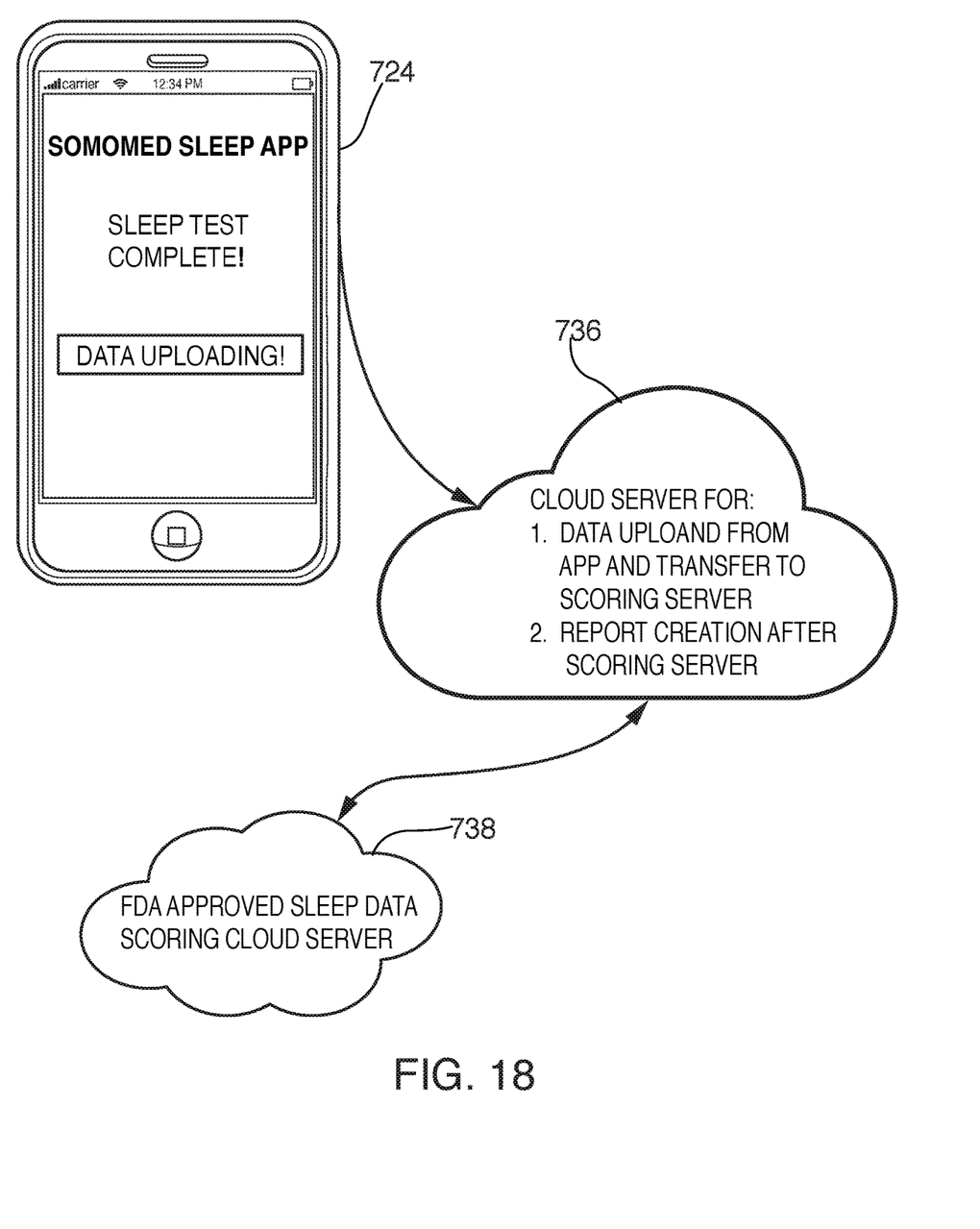
FIG. 18 is a flow diagram of a process in accordance with an embodiment of the present disclosure.

While the data is uploading at the status screen 724, also shown in FIG. 18, the data may be uploaded from the user's mobile phone in an encrypted fashion directly to a cloud server 736. The uploading can be carried out in any traditional fashion using wireless data signals transmitted over an internet connection. At the cloud server 736, the data may be checked for completeness and sent to an automatic scoring server, which may process or preprocess the data to determine whether any trends can be surmised form the data. This process may be carried out automatically. The observations of the scoring server may then be used to automatically compile a sleep report for the particular patient based on the particular data set that was provided, and the sleep report may be sent from the scoring server to an approved scoring server 738 for final validation of the conclusions. When the final validation is complete, the report may optionally be provided to a physician for final review and approval before being returned to the patient.

In this respect, in one aspect, the present disclosure describes transmitting the collected data securely and in an encrypted format to a cloud based FDA approved algorithmic software in order to analyze and mark specific sleep events within the patient's home sleep test. This algorithm will analyze events such as apnea hypopnea index, snoring, or cardiac events. The data from the scoring algorithm will then be transferred to a data report processing server. The server will compile the event data and automatically generate a template report showing patients clinic assessment from the sleep test. In certain alternative embodiments, which may include additional sensor types such as EKG pickups, heartrate monitors, motion sensors, temperature sensors, perspiration sensors and the like, the algorithmic software may be used to additionally diagnose or provide conclusions related to seizure and brain activity during sleep, intensity of dreams, cardiac-related issues, and others.

It is another object of the present disclosure to utilize the data report processing server to automatically assess data as calculated by the scoring server and determine a patient's level of Apnea severity. The typical categories will be no apnea, mild apnea, moderate apnea, and severe apnea. The server will automatically format a sample clinical report as shown below, which includes information and represents an exemplary report that can either be generated automatically by the system and approved by an attending physician or provided for reference directly to the patient.

SomnoMed Sleep App
PATIENT NAME: Smith, John
PATIENT #: fad-JS-54
DATE OF BIRTH: 1955-08-19
REFERRER: Bob Jones MD
DATE OF STUDY: 2018-05-25
DATE OF INTERPRETATION: 2018-05-30 18:14:43
INTERPRETING PHYSICIAN: William Smith MD
TECH: Adam Warrant HOME STUDY INTERPRETATION Physician Interpretation: Impressions
1. Severe obstructive sleep apnea syndrome
2. Snoring was recorded.
Recommendations
1. The patient should be scheduled for a therapeutic sleep study with CPAP/Bilevel titration.
2. Begin a medically supervised program to achieve and maintain ideal body weight.
3. Sleep in a non-supine position
4. Avoid bedtime alcohol and sedatives
5. Avoid operating heavy equipment
6. Avoid driving while feeling drowsy
Signed Electronically 2018-05-30 18:14:43
William Smith, M.D.
Pulmonary Disease/Sleep Medicine
Recommendation of this report should be communicated to the patient by the referring physician. The interpreting physician is available for questions regarding this report.

TECHNICAL REPORT:
Patient History:
Laura Smith is a 62 year old male who is 68 inches tall and weighs 185 pounds. The patient has a neck circumference of N/A inches, and a BMI of 27.8. The patient complaints include snoring and fatigue. The patient has an Epworth Sleepiness Scale score of 5/24, and is not a user of tobacco products.
Medications: None listed
Allergies: NKDA
Day of Study: Medications: None listed Nap: No
Alcohol: No
Caffeine: Yes
Protocol:
The study was performed using the SomnoMed system. The channels recorded were: Airflow acquired with a nasal pressure cannula. Oxygen saturation (SpO2) was monitored using a pulse oximeter. Thoracic respiratory movements were recorded by respiratory inductive plethysmography. The tracing was scored using 30 second epochs. Hypopneas were scored per AASM definition.
Position:
The patient slept in the supine, right side position(s).
Sleep Latency:
The patient's sleep onset latency after lights out was 0.0 minutes. The Stage R sleep latency from sleep onset was N/A minutes.
Total Sleep Time:
Because of the nature of a home sleep test, a 100% of the data is scored as Stage 2 sleep.
Respiratory:
The patient was observed to have had a total number of 74 apneas and hypopneas with an AHI index of 34.7 per hour during total sleep time. The normal AHI index is less than 5 per hour. There were 24 obstructive apneas, 0 mixed apneas, 9 central apneas, and 41 hypopneas.
Oxygenation:
The patient had an average oxygen saturation of 93%. The minimum oxygen level was 75%. Pulse Oximeters are accurate to a low SpO2 of 70% (+,−3).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims)

are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for conducting a sleep test, comprising:
   initiating a sleep test script, and providing the script to a patient;
   shipping testing hardware from a provider to the patient, and providing instructions to the patient for connecting the testing hardware to a mobile computing device;
   downloading and installing a mobile sleep application onto the mobile computing device;
   fitting the testing hardware onto a body of the patient, the testing hardware including an adjustable belt that is affixed around a torso of the patient;
   connecting the testing hardware to a sensor interface device using wired connections, connecting the sensor interface device to the mobile computing device, and mounting the sensor interface device onto the adjustable belt;
   conducting the sleep test using the mobile sleep application operating on the mobile computing device;
   collecting a data set during the test in a memory of the mobile computing device;
   validating, using the mobile sleep application, whether the data set collected in the memory of the mobile computing device was collected consistently during a sleep session;
   encrypting the data set in the mobile computing device and uploading the data set to a cloud server;
   validating with the cloud server the data set against the sleep test script and identifying information for the patient;
   automatically sorting, normalizing, and scoring the data set using a scoring algorithm that is stored and operates in the cloud server;
   generating a clinical report based on the data set using the scoring algorithm, the clinical report containing health condition diagnosis and recommendations that is automatically generated in the cloud server using the scoring algorithm based on the data set; and
   transmitting the clinical report from the cloud server directly to the mobile computing device such that the patient is permitted to access and review the clinical report.

2. The method of claim 1, wherein the testing hardware includes a plurality of external sensors, and wherein the method further comprises connecting the plurality of external sensors to the sensor interface device, and wherein connecting the sensor interface device to the mobile computing device is carried out such that signals or information provided from the plurality of external sensors is conveyed to the mobile computing device and is input into the mobile sleep application.

3. The method of claim 1, further comprising using at least one onboard sensor integrated with the mobile computing device during the sleep test.

4. The method of claim 1, wherein the testing hardware includes a breathing sensor, a nasal airflow sensor and a blood oxygen sensor.

5. The method of claim 3, wherein the at least one onboard sensor includes a microphone and an inertial sensor.

6. The method of claim 5, wherein the microphone is used to provide information relative to snoring during the sleep test, and wherein the inertial sensor is used to provide a patient position during the sleep test.

7. A method for conducting a sleep test for a patient at home, the method comprising:
   receiving at a provider a prescription from a physician relative to a patient for conducting a sleep test;
   collecting patient information at the provider relative to the patient;
   providing information to the patient from the provider relative to downloading and installing onto a mobile computing device of the patient a sleep monitoring mobile application;
   sending to the patient from the provider a set of testing hardware, the set of testing hardware including a plurality of external sensors, the plurality of external sensors including an adjustable belt having a breathing sensor, a nasal airflow sensor, and a blood oxygen sensor;
   sending to the patient a sensor interface device, the plurality of external sensors being connectable via wired connections to the sensor interface device, and the sensor interface device being connectable to the adjustable belt;
   wherein the patient is instructed to connect the set of testing hardware to the sensor interface device, informationally connect the sensor interface device to the mobile computing device, conduct a sleep test, and acquire a set of data that is stored in encrypted form within the sleep monitoring mobile application;
   validating, using the mobile sleep application, whether the set of data acquired within the sleep monitoring mobile application was collected consistently during a sleep session;

transmitting the set of data to a cloud server, validating with the cloud server the set of data against patient information and the prescription, and using an algorithm operating in the cloud server to automatically sort, normalize and score the set of data to automatically generate a clinical report, wherein the clinical report is based on the set of data and is compiled using the algorithm operating in the cloud server to contain health condition diagnoses and recommendations;

providing the report to physician for review and approval; and transmit the report from the physician to the patient using the sleep monitoring mobile application.

8. The method of claim 7, wherein the set of data further includes data acquired by at least one onboard sensor of the mobile computing device.

9. The method of claim 8, wherein the at least one onboard sensor includes a microphone and an inertial sensor.

10. The method of claim 9, wherein the microphone is used to provide information relative to snoring during the sleep test, and wherein the inertial sensor is used to provide a patient position during the sleep test.

* * * * *